US00PP20564P2

(12) United States Plant Patent
Kubota

(10) Patent No.: US PP20,564 P2
(45) Date of Patent: Dec. 15, 2009

(54) ***NEMESIA* PLANT NAMED 'GG PINK'**

(50) Latin Name: *Nemesia hybrida*
Varietal Denomination: GG Pink

(75) Inventor: Keiichi Kubota, Kanagawa (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/228,274

(22) Filed: Aug. 11, 2008

(51) Int. Cl.
*A01H 5/00* (2006.01)

(52) U.S. Cl. ..... Plt./458

(58) Field of Classification Search ..... Plt./458
See application file for complete search history.

*Primary Examiner*—June Hwu
(74) *Attorney, Agent, or Firm*—C. A. Whealy

(57) ABSTRACT

A new and distinct cultivar of *Nemesia* plant named 'GG Pink', characterized by its compact, upright and mounded growth habit; freely branching habit; freely flowering habit; long flowering period; dark pink-colored flowers; and good garden performance.

1 Drawing Sheet

Botanical designation: *Nemesia hybrida.*
Cultivar denomination: 'GG Pink'.

BACKGROUND OF THE INVENTION

The present invention relates to a new and distinct cultivar of *Nemesia*, botanically known as *Nemesia hybrida* and hereinafter referred to by the name 'GG Pink'.

The new *Nemesia* plant is a product of a planned breeding program conducted by the Inventor in Hiratuka, Kanagawa, Japan. The objective of the breeding program is to create new compact, mounding and freely-branching *Nemesia* cultivars with attractive flower coloration.

The new *Nemesia* plant originated from a cross-pollination made by the Inventor in November, 2005 in Hiratuka, Kanagawa, Japan of a proprietary selection of *Nemesia hybrida* identified as code number TNP-4, not patented, as the female, or seed, parent with *Nemesia hybrida* 'Peach Doll', not patented, as the male, or pollen, parent. The new *Nemesia* was discovered and selected by the Inventor as a single flowering plant within the progeny of the stated cross-pollination in a controlled greenhouse environment in Hiratuka, Kanagawa, Japan in April, 2006.

Asexual reproduction of the new *Nemesia* plant by vegetative cuttings in a controlled environment in Hiratuka, Kanagawa, Japan since May, 2006, has shown that the unique features of this new *Nemesia* are stable and reproduced true to type in successive generations.

SUMMARY OF THE INVENTION

Plants of the new *Nemesia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'GG Pink'. These characteristics in combination distinguish 'GG Pink' as a new and distinct cultivar of *Nemesia:*

1. Compact, upright and mounded growth habit.
2. Freely branching habit.
3. Freely flowering habit.

4. Long flowering period.
5. Dark pink-colored flowers.
6. Good garden performance.

Plants of the new *Nemesia* can be compared to plants of the female parent selection. Plants of the new *Nemesia* differ from plants of the female parent selection primarily in flower color as plants of the female parent selection have light pink-colored flowers.

Plants of the new *Nemesia* can be compared to plants of the male parent, 'Peach Doll'. Plants of the new *Nemesia* differ from plants of 'Peach Doll' in the following characteristics:

1. Plants of the new *Nemesia* are more compact and mounding than plants of 'Peach Doll'.
2. Plants of the new *Nemesia* are more freely branching than plants of 'Peach Doll'.

Plants of the new *Nemesia* can also be compared to plants of 'Mellow Dessert Peach', not patented. In side-by-side comparisons conducted by the Inventor in Hiratuka, Kanagawa, Japan, plants of the new *Nemesia* differed from plants of 'Mellow Dessert Peach' in the following characteristics:

1. Plants of the new *Nemesia* were more compact and mounding than plants of 'Mellow Dessert Peach'.
2. Plants of the new *Nemesia* were more freely branching than plants of 'Mellow Dessert Peach'.
3. Plants of the new *Nemesia* had smaller leaves than plants of 'Mellow Dessert Peach'.
4. Plants of the new *Nemesia* are more freely flowering than plants of 'Mellow Dessert Peach'.

BRIEF DESCRIPTION OF THE PHOTOGRAPHS

The accompanying colored photographs illustrate the overall appearance of the new *Nemesia* plant, showing the colors as true as it is reasonably possible to obtain in colored reproductions of this type. Colors in the photographs may differ slightly from the color values cited in the detailed botanical description which accurately describe the colors of the new *Nemesia.*

The photograph at the top of the sheet comprises a side perspective view of a typical flowering plant of 'GG Pink' grown in a container.

The photograph at the bottom of the sheet is a close-up view of typical flowers of 'GG Pink'.

DETAILED BOTANICAL DESCRIPTION

The aforementioned photographs and following observations, measurements and values describe plants grown in Hiratuka, Kanagawa, Japan, under commercial practice during the winter and early spring in a glass-covered greenhouse with day temperatures ranging from 12° C. to 20° C. and night temperatures ranging from 5° C. to 8° C. Plants had been growing for four months when the photographs and description were taken. In the following description, color references are made to The Royal Horticultural Society Colour Chart, 2001 Edition, except where general terms of ordinary dictionary significance are used.

Botanical classification: *Nemesia hybrida* 'GG Pink'.

Parentage:

*Female, or seed, parent.*—Proprietary selection of *Nemesia hybrida* identified as code number TNP-4, not patented.

*Male, or pollen, parent.*—*Nemesia hybrida* 'Peach Doll', not patented.

Propagation:

*Type.*—By vegetative cuttings.

*Time to initiate roots.*—About one week at temperatures of 20° C. to 25° C.

*Time to produce a rooted young plant.*—About 20 days at temperatures of 15° C. to 20° C.

*Root description.*—Fibrous; white in color.

*Rooting habit.*—Freely branching; moderately dense.

Plant description:

*Plant and growth habit.*—Compact, upright and mounded growth habit. Freely branching with two lateral branches potentially forming at every node. Vigorous growth habit.

*Plant height.*—About 15 cm.

*Plant diameter.*—About 25.7 cm.

Lateral branch description:

*Length.*—About 6 cm.

*Diameter.*—About 1.5 mm.

*Internode length.*—About 1.3 cm.

*Strength.*—Strong; flexible.

*Aspect.*—Upright to somewhat outwardly spreading.

*Texture.*—Smooth, glabrous.

*Color.*—Close to 144A.

Foliage description:

*Arrangement.*—Opposite, simple.

*Length.*—About 1.7 cm.

*Width.*—About 9 mm.

*Shape.*—Lanceolate.

*Apex.*—Acute.

*Base.*—Obtuse.

*Margin.*—Serrate.

*Texture, upper and lower surfaces.*—Smooth, glabrous.

*Venation pattern.*—Pinnate, reticulate.

*Color.*—Developing and fully expanded leaves, upper surface: Close to 137B; venation, close to 144B. Developing and fully expanded leaves, lower surface: Close to 138B; venation, close to 144B.

*Petioles.*—Length: About 1.1 mm. Diameter: About 2.3 mm. Texture, upper and lower surfaces: Smooth, glabrous. Color, upper and lower surfaces: Close to 144B.

Flower description:

*Flower arrangement and habit.*—Bilabiate solitary flowers arranged on termnal racemes; flowering acropetally towards the apex; flowers facing upright to outwardly. Freely flowering habit with about seven flowers per raceme and about 33 racemes per plant.

*Fragrance.*—Faint, pleasant.

*Natural flowering season.*—In Japan, plants flower from late summer to early autumn; flowering continuous during this period. Flowers begin flowering about three months after planting.

*Flower longevity.*—Flowers last about five to seven days on the plant; flowers not persistent.

*Inflorescence height.*—About 7.6 cm.

*Inflorescence diameter.*—About 4 cm.

*Flower diameter.*—About 2 cm by 1.7 cm.

*Flower depth.*—About 1.2 cm.

*Tube length.*—About 1.8 mm.

*Tube diameter.*—About 2.5 mm.

*Flower buds.*—Shape: Obovate. Length: About 8.8 mm. Diameter: About 4.2 mm. Color: Close to 70C.

*Petals.*—Arrangement: Five modified petals; four upper petals fused forming an upright lobed and arched banner lip; lower petal modified into a larger lip with convex oval protuberance serving as a nectar guide and insect landing platform. Shape, upper lip: Elliptic. Shape, lower lip: Cordate. Apex, upper lip: Rounded. Apex, lower lip: Cordate. Margin, upper lip: Entire. Margin, lower lip: Entire; slightly undulate. Length, upper lip: About 1.1 cm. Length, lower lip: About 9.7 mm. Width, upper lip: About 3 mm to 6 mm. Width, lower lip: About 1 cm. Texture, upper and lower lips, upper and lower surfaces: Smooth, glabrous. Color, upper lip: When opening, upper surface: Close to 70B; towards the throat, close to 76D. When opening, lower surface: Close to N74D. Fully opened, upper surface: Close to 70B; towards the throat, close to 76D. Fully opened, lower surface: Close to 75C. Color, lower lip: When opening, upper surface: Close to 70B; nectar guide, close to 4B. When opening, lower surface: Close to 75C. Fully opened, upper surface: Close to 70B; nectar guide, close to 11D. Fully opened, lower surface: Close to 75C. Color, throat and tube: Close to 144D.

*Spur.*—Length: About 7.5 mm. Diameter: About 2 mm. Color: Close to 157B.

*Sepals.*—Arrangement: Calyx star-shaped with five sepals fused at the base. Shape: Lanceolate. Apex: Acute. Margin: Entire. Length: About 2.9 mm. Width: About 1.5 mm. Texture, upper and lower surfaces: Pubescent. Color, upper and lower surfaces: Close to 138A.

*Peduncles.*—Length: About 2 cm. Diameter: About 1.5 mm. Strength: Moderately strong; flexible. Texture: Smooth, glabrous. Color: Close to 144A.

*Pedicels.*—Length: About 1.2 cm. Diameter: About 0.5 mm. Strength: Moderately strong; flexible. Texture: Pubescent. Color: Close to 144A.

*Reproductive organs.*—Stamens: Quantity/arrangement: Four per flower. Stamen length: About 1.5 mm to 3.2 mm. Anther shape: Narrowly elliptic. Anther size: About 2 mm by 0.4 mm. Anther color: Close to 8A. Pollen amount: Moderate. Pollen color: Close to 8B. Pistils: Quantity: One per flower. Pistil length: About 2.8 mm. Style color: Close to 145D. Stigma shape: Ovate. Stigma color: Close to 145D. Ovary color: Close to 143C. Seed/fruit: Seed and fruit development have not been observed on plants of the new *Nemesia*.

Pathogen/pest resistance: Plants of the new *Nemesia* have not been observed to be resistant to pests and pathogens common to *Nemesia*.

Garden performance: Plants of the new *Nemesia* have been observed have good garden performance and to tolerate wind, rain and temperatures ranging from 5° C. to 35° C.

It is claimed:

1. A new and distinct *Nemesia* plant named 'GG Pink' as illustrated and described.

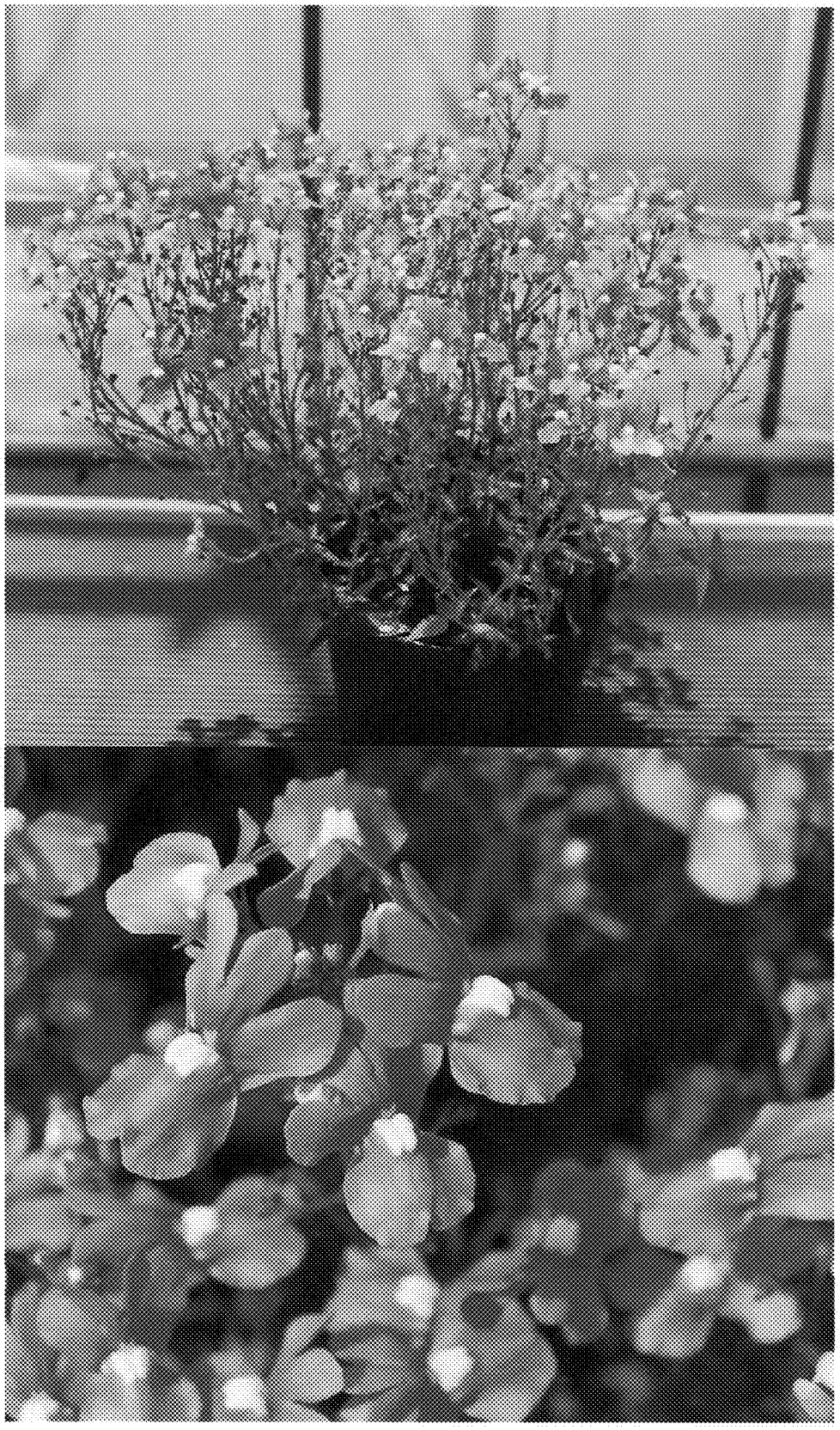

* * * * *